United States Patent
Shersher et al.

(10) Patent No.: US 12,337,122 B2
(45) Date of Patent: Jun. 24, 2025

(54) BODY CAVITY IRRIGATION AND DRAINAGE SYSTEM

(71) Applicant: The Cooper Health System, a New Jersey Non-Profit Corporation, Camden, NJ (US)

(72) Inventors: David D. Shersher, Philadelphia, PA (US); Wissam Abouzgheib, Cherry Hill, NJ (US)

(73) Assignee: The Cooper Health System, a New Jersey Non-Profit Corporation

( * ) Notice: Subject to any disclaimer, the term of this patent is extended or adjusted under 35 U.S.C. 154(b) by 0 days.

(21) Appl. No.: 17/871,460

(22) Filed: Jul. 22, 2022

(65) Prior Publication Data

US 2022/0355083 A1 Nov. 10, 2022

Related U.S. Application Data

(63) Continuation of application No. 16/566,077, filed on Sep. 10, 2019, now Pat. No. 11,426,559.

(Continued)

(51) Int. Cl.
*A61M 25/00* (2006.01)
*A61B 17/34* (2006.01)
(Continued)

(52) U.S. Cl.
CPC ..... *A61M 25/0074* (2013.01); *A61B 17/3415* (2013.01); *A61M 1/71* (2021.05);
(Continued)

(58) Field of Classification Search
CPC ...... A61M 25/0074; A61M 1/71; A61M 1/77; A61M 1/84; A61M 1/85; A61M 25/04;
(Continued)

(56) References Cited

U.S. PATENT DOCUMENTS

| 4,983,168 A | 1/1991 | Moorehead |
| 5,002,528 A | 3/1991 | Palestrant |

(Continued)

FOREIGN PATENT DOCUMENTS

| CN | 201930375 | 8/2011 |
| CN | 201930375 U | 8/2011 |

(Continued)

OTHER PUBLICATIONS

Supplementary European Search Report EP19859047 mailed on Oct. 5, 2021.

(Continued)

*Primary Examiner* — Robert J Utama
*Assistant Examiner* — Hamza A Darb
(74) *Attorney, Agent, or Firm* — The Belles Group, P.C.

(57) ABSTRACT

A body cavity irrigation and drainage system including a catheter apparatus that has a proximal end, a distal end, a longitudinal axis, a first flow channel extending from the proximal end to the distal end, and a second flow channel extending from the proximal end to the distal end and being fluidly isolated from the first flow channel. The catheter apparatus may alterable between: (1) a first state in which the first and second flow channels are linear and parallel to the longitudinal axis along an entire length of the first and second flow channels; and (2) a second state in which a distal portion of the first flow channel curls away from the longitudinal axis in a first direction and a distal portion of the second flow channel curls away from the longitudinal axis in a second direction that is different from the first direction.

20 Claims, 9 Drawing Sheets

Related U.S. Application Data

(60) Provisional application No. 62/729,689, filed on Sep. 11, 2018.

(51) Int. Cl.
*A61M 1/00* (2006.01)
*A61M 25/04* (2006.01)
*A61M 25/06* (2006.01)

(52) U.S. Cl.
CPC ............... *A61M 1/77* (2021.05); *A61M 1/84* (2021.05); *A61M 1/85* (2021.05); *A61M 25/04* (2013.01); *A61M 25/0668* (2013.01); *A61B 2217/007* (2013.01); *A61M 2025/0681* (2013.01); *A61M 2202/0492* (2013.01)

(58) Field of Classification Search
CPC ...... A61M 25/0668; A61M 2025/0681; A61M 2202/0492; A61M 2210/101; A61B 17/3415; A61B 2217/007
See application file for complete search history.

(56) References Cited

U.S. PATENT DOCUMENTS

| | | |
|---|---|---|
| 5,618,271 A | 4/1997 | Yoon |
| 5,634,934 A | 6/1997 | Yoon |
| 5,865,802 A | 2/1999 | Yoon et al. |
| 6,582,390 B1 | 6/2003 | Sanderson |
| 7,465,286 B2 | 12/2008 | Patterson et al. |
| 7,824,384 B2 | 11/2010 | Watson, Jr. |
| 7,909,798 B2 | 3/2011 | Osypka |
| 8,105,309 B2 | 1/2012 | Kassab et al. |
| 8,702,662 B2 | 4/2014 | Boyle |
| 8,932,316 B2 | 1/2015 | Keast et al. |
| 9,480,782 B2 | 11/2016 | Burrow |
| 9,597,159 B2 | 3/2017 | Boyle, Jr. |
| 2005/0107736 A1 | 5/2005 | Landman et al. |
| 2006/0200079 A1* | 9/2006 | Magnusson ....... A61M 25/0017 604/164.13 |
| 2007/0255222 A1 | 11/2007 | Li et al. |
| 2008/0027334 A1 | 1/2008 | Langston |
| 2009/0204052 A1* | 8/2009 | Nimkar ............. A61M 25/0009 604/523 |
| 2010/0049171 A1 | 2/2010 | McQueen et al. |
| 2011/0098682 A1 | 4/2011 | Ahmed et al. |
| 2012/0184942 A1* | 7/2012 | Lareau ............. A61M 25/0102 604/540 |
| 2016/0310699 A1* | 10/2016 | Ai-Jilaihawi .......... A61B 8/481 |
| 2017/0348512 A1* | 12/2017 | Orr ........................ A61M 1/75 |

FOREIGN PATENT DOCUMENTS

| | | |
|---|---|---|
| CN | 107050628 A | 8/2017 |
| WO | WO9617644 A1 | 6/1996 |

OTHER PUBLICATIONS

International Search Report and Written Opinion for International Application No. PCT/US19/50354 mailed on Nov. 22, 2019.

* cited by examiner

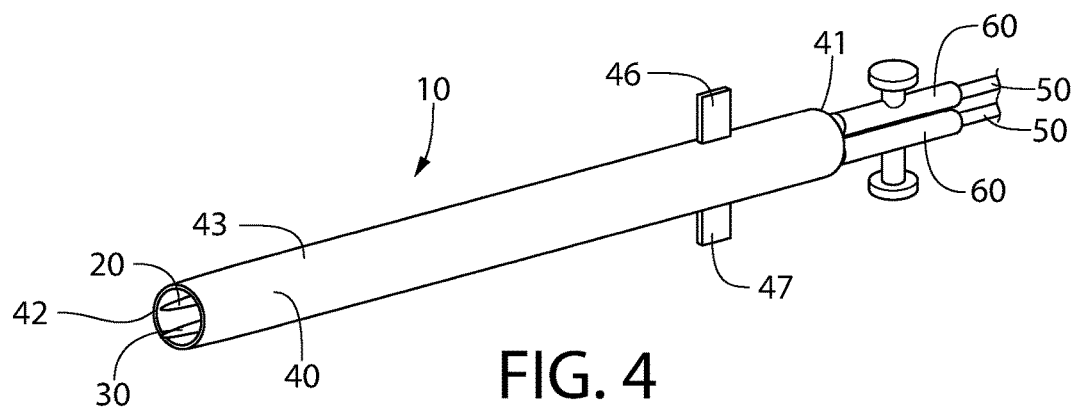
FIG. 4
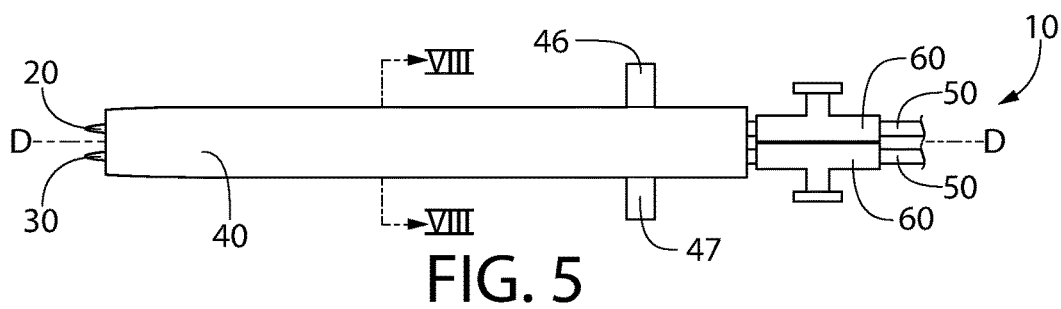
FIG. 5
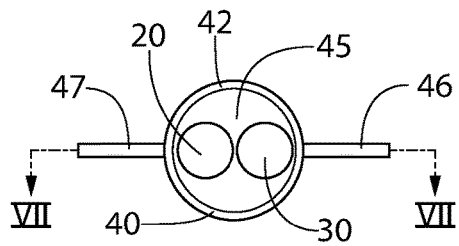
FIG. 6
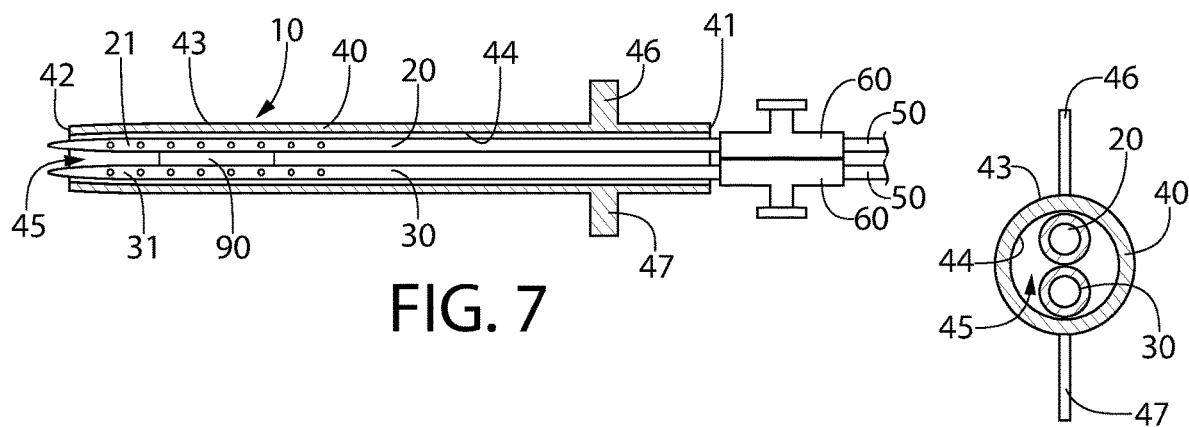
FIG. 7
FIG. 8

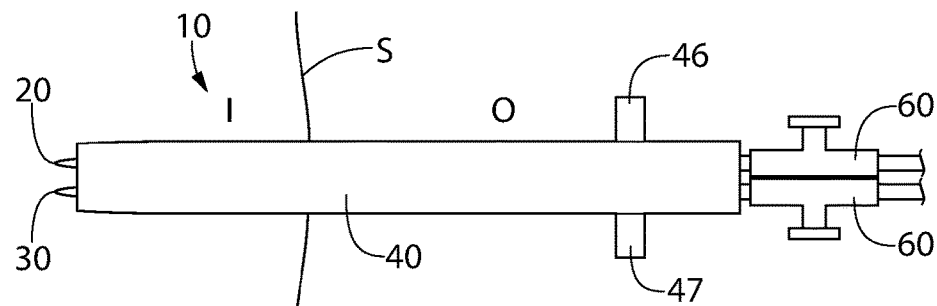
FIG. 9
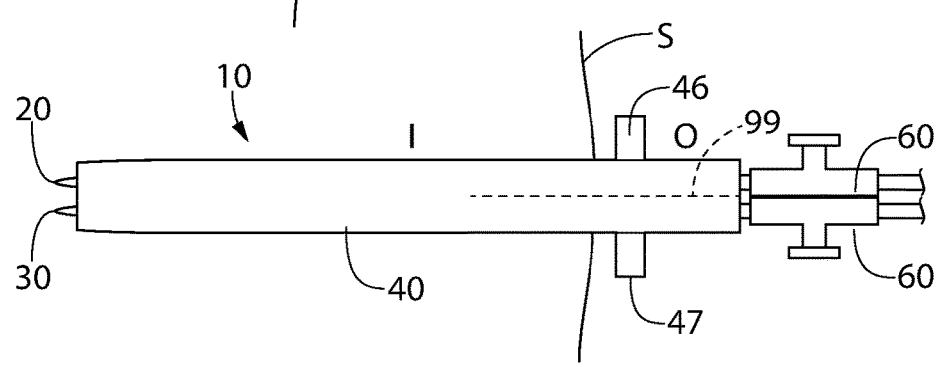
FIG. 10
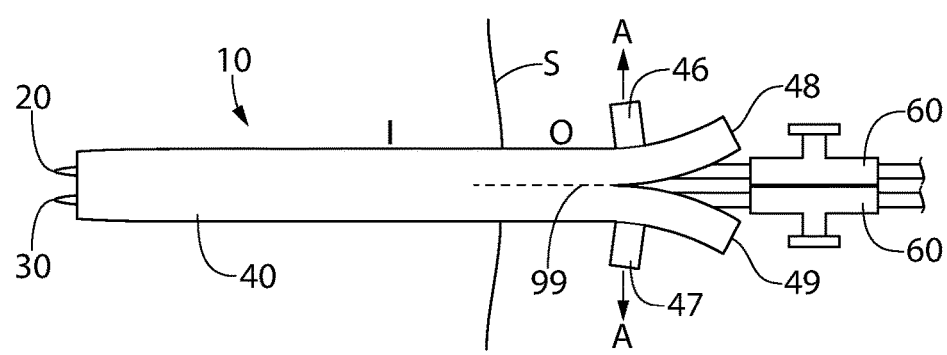
FIG. 11
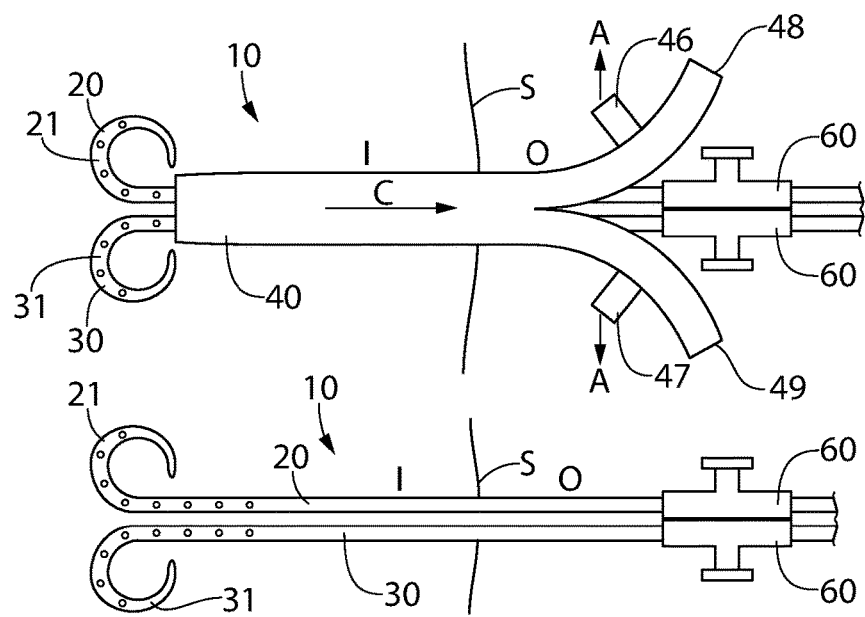
FIG. 12
FIG. 13

BODY CAVITY IRRIGATION AND DRAINAGE SYSTEM

CROSS-REFERENCE TO RELATED APPLICATIONS

The present application is a continuation of U.S. patent application Ser. No. 16/566,077, filed Sep. 10, 2019, now U.S. Pat. No. 11,426,559 issued on Aug. 30, 2022, which claims priority to U.S. Provisional Patent Application Ser. No. 62/729,689, filed Sep. 11, 2018, the entireties of which are incorporated herein by reference.

FIELD

The present invention relates to the field of medicine. Particular embodiments of the invention relate to irrigating and draining fluid from the pleural space.

BACKGROUND

The pleural space is the space between the two layers of the pleura, the thin covering that protects and cushions the lungs. A pleural effusion is a buildup of fluid in the pleural space. One kind of pleural effusion is pleural empyema. Pleural empyema is a collection of pus in the pleural cavity caused by microorganisms, usually bacteria. Often pleural empyema happens in the context of pneumonia, injury, or chest surgery. It is important to remove this pus from the pleural space in order to control or eliminate the infection. Another type of pleural effusion is a hemothorax, or a collection of blood in the pleural space. If this is left in place, it can create a thick peel around the lung called a fibrothorax, potentially affecting breathing. Some methods of removing fluid from body cavities can be ineffective in the case of pleural empyema or hemothorax due to the viscous nature of the fluid. Even those methods of removing highly viscous fluids from body cavities that have seen success are cumbersome and/or require surgery or the use of large bore chest tubes.

Accordingly, improved systems and methods for irrigating and draining highly viscous fluids from the pleural space are needed.

SUMMARY

In one aspect, the invention is directed to a system, or part of a system, that effectively removes viscous fluid from a body cavity using only one entry point into the body cavity. An example used to describe embodiments of the invention is a system for removing the pus of a pleural empyema or blood of a hemothorax. However, it is noted that systems and methods of the invention can be used to remove many types of fluids from many types of biological and non-biological cavities.

In one aspect, the invention may be a body cavity irrigation and drainage system comprising: a first pigtail catheter comprising a first body portion that extends along a first longitudinal axis and a first tail portion, the first pigtail catheter being alterable between: (1) a first state in which the first tail portion extends along the first longitudinal axis; and (2) a second state in which the first tail portion curls away from the first longitudinal axis in a first direction; a second pigtail catheter comprising a second body portion that extends along a second longitudinal axis and a second tail portion, the second pigtail catheter being alterable between: (1) a first state in which the second tail portion extends along the second longitudinal axis; and (2) a second state in which the second tail portion curls away from the second longitudinal axis in a second direction that is different from the first direction; and wherein the first body portion of the first pigtail catheter is coupled to the second body portion of the second pigtail catheter to maintain the first and second pigtail catheters in a fixed relative orientation.

In another aspect, the invention may be a body cavity irrigation and drainage system comprising: a sheath comprising a cavity, wherein the sheath is configured to be inserted into a body cavity through a single incision; a first pigtail catheter positioned in the cavity of the sheath; and a second pigtail catheter positioned in the cavity of the sheath.

In yet another aspect, the invention may be a method of irrigating and draining a body cavity, the method comprising: cutting an incision in a patient; inserting a first pigtail catheter and a second pigtail catheter through the incision so that at least a first tail portion of the first pigtail catheter and a second tail portion of the second pigtail catheter are located within a body cavity of the patient; allowing the first tail portion of the first pigtail catheter to curl in a first direction and allowing the second tail portion of the second pigtail catheter to curl in a second direction that is different than the first direction; coupling the first pigtail catheter to an irrigation source so that a fluid can be introduced into the body cavity through the first pigtail catheter; and coupling the second pigtail catheter to a suction source so that suction can be applied to the body cavity through the second pigtail catheter.

In still another aspect, the invention may be a body cavity irrigation and drainage system comprising: a catheter apparatus comprising: a body comprising a longitudinal axis and an inner surface that defines a cavity; an internal wall located within the cavity that divides the cavity into a first flow channel and a second flow channel; wherein a distal end of the body is alterable between: (1) a first state in which the distal end is elongated along the longitudinal axis; and (2) a second state in which the distal end is separated into a first tail portion that curls away from the longitudinal axis in a first direction and a second tail portion that curls away from the longitudinal axis in a second direction that is opposite the first direction.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is a perspective view of a body cavity irrigation and drainage system comprising a sheath and first and second pigtail catheters in accordance with an exemplary embodiment of the invention;

FIG. 5 is a side view of the system of FIG. 4;

FIG. 6 is an end view of the system of FIG. 4;

FIG. 7 is a sectional view along section line VII-VII in FIG. 6;

FIG. 8 is a sectional view along section line VIII-VIII in FIG. 5;

FIGS. 9 and 10 are a schematic side views of the system of FIG. 4 being inserted into a body cavity of a patient;

FIGS. 11-13 are schematic side views of the sheath being torn and removed from the patient while the first and second pigtail catheters remain in the body cavity of the patient;

Figure 1A:
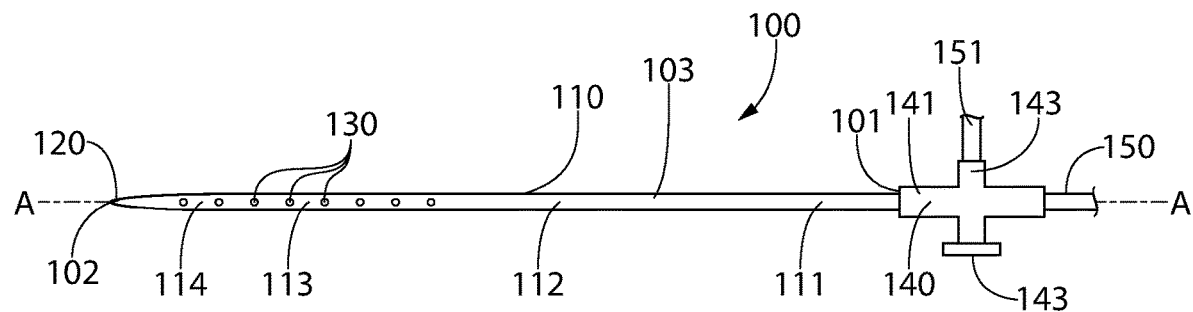
FIG. 1A is a side view of a pigtail catheter in a first state wherein a tail portion thereof is straight.

All drawings are schematic and not necessarily to scale. Parts given a reference numerical designation in one FIG. may be considered to be the same parts where they appear in other FIGS. without a numerical designation for brevity unless specifically labeled with a different part number and described herein.

DETAILED DESCRIPTION

The following description of the preferred embodiment(s) is merely exemplary in nature and is in no way intended to limit the invention, its application, or uses.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "connected," "coupled," "interconnected," and similar refer to a relationship wherein structures are secured or attached to one another either directly or indirectly through intervening structures, as well as both movable or rigid attachments or relationships, unless expressly described otherwise. The term "fixed" refers to two structures that cannot be separated without damaging one of the structures. The term "filled" refers to a state that includes completely filled or partially filled.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The present disclosure relates to a system, or part of a system, that effectively irrigates and removes viscous fluid from a body cavity using only one entry point into the body cavity. An example used to describe embodiments of the invention is a system for removing the pus of a pleural empyema or blood of a hemothorax. The present disclosure also relates to a method of irrigating and draining a body cavity.

Figure 1B:
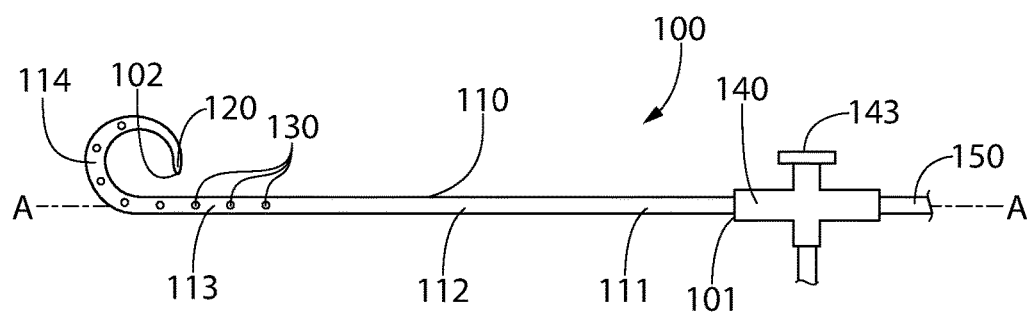
FIG. 1B is a side view of the pigtail catheter of FIG. 1A in a second state wherein the tail portion thereof is curved.
Figure 2:
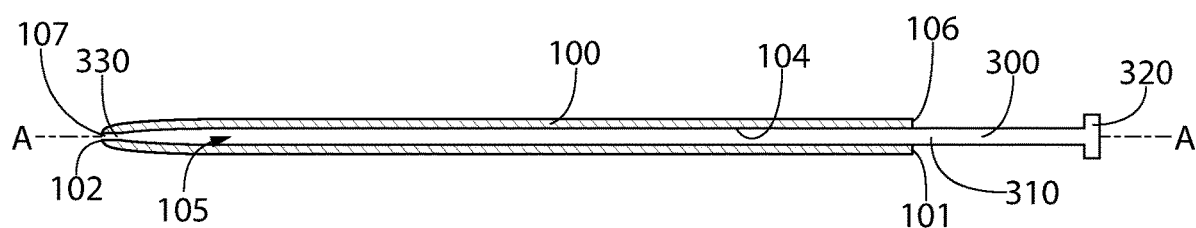
FIG. 2 is a partial sectional view of a pigtail catheter with a cannula disposed therein to force the pigtail catheter into the first state.

Referring to FIGS. 1A, 1B, and 2 concurrently, a pigtail catheter 100 is illustrated and will be described. The pigtail catheter 100 is a conventional and well-known medical device that is commonly used for draining unwanted body fluids from an organ, duct, or abscess. Pigtail catheters are frequently inserted into a body cavity of a patient using a Seldinger technique, which is a medical procedure that includes: (1) puncturing the skin of a patient with a sharp needle; (2) advancing a guidewire through the lumen of the needle and into a body cavity of the patient; (3) withdrawing the needle; (4) passing a dilater over the guidewire to expand the size of the incision in the skin and then removing the dilater; (5) inserting a pigtail catheter into the body cavity of the patient by passing the pigtail catheter over the guidewire, wherein during the insertion process a cannula or trocar or introducer is positioned within the passageway/channel of the pigtail catheter to maintain the pigtail catheter in a straightened state (FIG. 1A); (6) removing the guidewire from the patient; and (7) removing the cannula or trocar from the pigtail catheter to allow the pigtail catheter to transition into its natural, curved state (FIG. 1B). Steps (6) and (7) may be accomplished simultaneously in some embodiments. Some steps may be provided out of order or may be omitted. Once the cannular or trocar is removed from the pigtail catheter, the catheter is maintained in place within the body cavity due to the curving of its tail end and the catheter may also be sutured to the patient's skin. Finally, the pigtail catheter may be operably coupled to a suction source to drain fluids from the body cavity and/or the pigtail catheter may be operably coupled to an irrigation source to irrigate the body cavity.

The pigtail catheter 100 comprises a body portion 110 that extends from a proximal end 101 to a distal end 102 along a longitudinal axis A-A. The pigtail catheter 100 comprises an outer surface 103 and an inner surface 104, the inner surface 104 defining a channel 105 that extends from the proximal end 101 to the distal end 102. There is a first opening 106 at the proximal end 101 and a second opening 107 at the distal end 102 so that the pigtail catheter 100 can be passed over a guidewire during insertion of the pigtail catheter 100 into a body cavity of a patient as described above. Fluids may also pass through the second opening 107 during irrigation and/or drainage of a body cavity as described herein.

The pigtail catheter 100 (or the body portion 110 thereof) generally comprises a proximal portion 111, a middle portion 112, and a distal portion 113, with the proximal portion 111 comprising the proximal end 101, the distal portion 113 comprising the distal end 102, and the middle portion 112 extending between the proximal end distal portions 111, 113. The pigtail catheter 100 comprises a plurality of apertures 130 in the distal portion 113, each of the apertures 130 extending through the body portion 110 from the outer surface 103 to the inner surface 104. Although there are no apertures in the middle and proximal portions 111, 112 in the exemplified embodiment, there may be apertures in those portions in some alternative embodiments. The apertures 130 are arranged in a spaced apart manner and are sized and configured to enable fluids to flow into and out of the channel 105 during various medical procedures. Thus, for example, during an irrigation procedure, a fluid can be passed into the channel 105 through the first opening 106 and the fluid can pass into the body cavity for irrigation/flushing via the apertures 130 and the second opening 107. During a draining procedure, suction can be applied to the pigtail catheter 100 so that fluids can be suctioned into the pigtail catheter 100 through the apertures 130 and the second opening 107.

The distal portion 113 of the body portion 110 of the pigtail catheter 100 also comprises a tail portion 114. The tail portion 114 is the distal-most part of the distal portion 113 and it includes the distal end 102. The tail portion 114 is alterable between a first state (FIG. 1A) in which the tail portion 114 is elongated along the longitudinal axis A-A of the body portion 110 and a second state (FIG. 1B) in which the tail portion 114 curls away from the longitudinal axis A-A. Specifically, in the second state the tail portion 114 extends away from the longitudinal axis A-A in a particular direction and then curls back upon itself in a spiral-like shape. The tail portion 114 may curl in a full revolution, less than a full revolution, or more than one full revolution in various different embodiments dependent upon the manner in which the pigtail catheter 100 is manufactured. In its natural state where no forces are being applied onto the tail portion 114, the tail portion 114 is in the second (i.e., curled) state. Forces must be applied onto the tail portion 114 to alter the tail portion 114 from the curled state into the first (straightened) state.

For example, as shown in FIG. 2, a device such as a cannula or a trocar or an introducer 300 is inserted into the channel 105 of the pigtail catheter 100. The cannula 300 is preferably formed of a rigid material such as metal, hard plastic, or the like. Furthermore, in the exemplified embodiment the cannula 300 has a main body 310, a tip 330, and a gripping feature 320. The gripping feature 320 may be gripped by the user to allow the user to pull cannula 300 out of and away from pigtail catheter 100 once it is properly positioned within a patient. Due to its rigidity, as the cannula 300 is inserted into the channel 105 from the first opening 106 in the proximal end 101 towards the second opening 107 in the distal end 102, the cannula 300 forces the tail portion 114 to transition from the curved state (FIG. 1B) to the straightened state (FIGS. 1A and 2).

During insertion of the pigtail catheter 100 into the body cavity of a patient, the tail portion 114 thereof should be in the second straightened state. Thus, oftentimes during this insertion procedure the cannula 300 is disposed within the channel 105 of the pigtail catheter 100 to ensure that the tail portion 114 thereof is maintained in the straightened state. The cannula 300 can be removed from the channel 105 of the pigtail catheter 100 after the pigtail catheter 100 is properly positioned within the body cavity of the patient to allow the tail portion 114 thereof to transition into its natural, curved state. In the curved state of the tail portion 114, the pigtail catheter 100 is held in place. Specifically, the curved shape can create resistance to accidental withdrawal of the pigtail catheter 100 from the patient. Furthermore, the curling of the tail portion 114, which includes many of the apertures 130 through which fluid may be injected into and removed from the body cavity, slows the flow of fluids injected therethrough so that the fluids do not burst out in a jet and cause injuries or obscure a medical imaging study.

In certain embodiments, the proximal end 101 of the pigtail catheter 100 may be operably coupled to a source of fluid or suction or both. To achieve this coupling, a valve 140 may be coupled to the proximal end 101 of the pigtail catheter 100. The valve 140 may be a 3-way stopcock in some embodiments, although other styles and types of valves including a two-way valve could be used in other embodiments. The valve 140 comprises a first port 141 that is connected to the proximal end 101 of the pigtail catheter 100, a second port 142 that is connected to a first tube or conduit 150, and a third port 143 that is connected to a second tube or conduit 152. The other end of the first tube 150 may be coupled to a source of suction and the other end of the second tube 151 may be coupled to an irrigation source. In other embodiments, the valve 140 may be a two-way valve and only one tube may extend from the valve 140 to a source of suction and/or irrigation or to a machine configured to apply suction or irrigation. The valve 140 also comprises an actuator 143 that enables a user to adjust the valve 140 to determine whether fluid will flow through the first and second ports 141, 142, through the first and third ports 141, 143, or through none of the ports. The valve 140 can be a shut off valve that permits the user to stop and/or throttle the supply of, for example, irrigation fluid and/or suction.

In some embodiments, the cannula 300 may be removed before the valve 140 is connected to the pigtail catheter 100. In other embodiments, the valve 140 may be constructed, for example, as a ball valve, such that the cannula 300 can extend through the valve 140 when the valve 140 is in the open position.

Figure 3A:
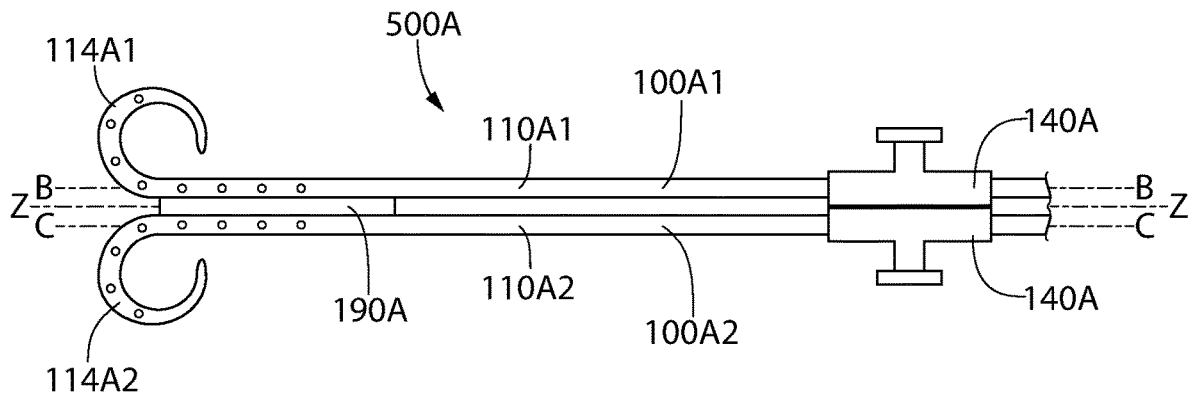
FIG. 3A is a side view of a catheter device that includes a first pigtail catheter and a second pigtail catheter that are coupled together in accordance with an embodiment of the present invention.

FIG. 3A illustrates a catheter device 500A in accordance with an embodiment of the present invention. The catheter device 500A extends along a longitudinal axis Z-Z. Moreover, the catheter device 500A comprises a first pigtail catheter 100A1 that extends along a first longitudinal axis B-B and a second pigtail catheter 100A2 that extends along a second longitudinal axis C-C. The first and second pigtail catheters 100A1, 100A2 are identical to the pigtail catheter 100 described above and thus they will not be described herein again in the interest of brevity, although some features thereof will be mentioned below to provide a full understanding of the inventive catheter device 500. Each of the pigtail catheters 100A1, 100A2 is coupled to a valve 140A, 140A that can be a two-way, three-way, or other style valve as needed for a particular purpose and as described above.

The first pigtail catheter 100A1 comprises a first body portion 110A1 that extends along the first longitudinal axis B-B and a first tail portion 114A1. The first tail portion 114A1 is alterable between a first state (i.e., straightened state) in which the first tail portion 114A1 extends along the first longitudinal axis B-B and a second state (i.e., a curled or curved state) in which the first tail portion 114A1 curls away from the first longitudinal axis B-B in a first direction. The second pigtail catheter 100A2 comprises a second body portion 110A2 that extends along the second longitudinal axis C-C and a second tail portion 114A2. The second tail portion 114A2 is alterable between a first state (i.e., straightened state) in which the second tail portion 114A2 extends along the second longitudinal axis C-C and a second state (i.e., curled or curved state) in which the second tail portion 114A2 curls away from the second longitudinal axis C-C in a second direction. The first and second pigtail catheters 100A1, 100A2 are illustrated in the second state in FIG. 3A.

Although the first and second pigtail catheters 100A1, 100A2 are not shown in cross-section, it should be appreciated that each comprises a channel or flow channel therein identical to the channel 105 of the pigtail catheter 100 described above. Because the first and second pigtail catheters 100A1, 100A2 are separate and distinct components, they each have a channel that is distinct from the other. Thus, if suction is applied to the first pigtail catheter 100A1, the suction will pull fluids from the body cavity through the channel of the first pigtail catheter 100A1 but not through the channel second pigtail catheter 100A2, and vice versa. Thus, the channels of the first and second pigtail catheters 100A1, 100A2 are independent and distinct from one another.

As shown in FIG. 3A, the first and second pigtail couplers 100A1, 100A2 are coupled together by a coupling device 190A. The coupling device 190A can be any device that can be utilized to couple the first and second pigtail catheters 100A1, 100A2 to one another. It is preferable that the coupling device 190A couple the first body portion 110A1 of the first pigtail catheter 100A1 to the second body portion 110A2 of the second pigtail catheter 100A2. Specifically, the coupling device 190A should not couple the first and second tail portions 114A1, 114A2 to one another because that could interfere with the ability of the tail portions 114A1, 114A2 to transition between the straight and curled states. Thus, the coupling device 190A should couple the first and second pigtail catheters 100A1, 100A2 to one another at a location that is between the tail portions 114A1, 114A2 and the proximal end of the pigtail catheters 100A1, 100A2.

As mentioned above, the coupling device 190A could be any device capable of coupling the first and second pigtail catheters 100A1, 100A2 to one another. For example, the coupling device 190A could be a series of fasteners such as screws, nails, or the like. In other embodiments, the coupling device 190A may comprise an adhesive, a clamp, a sleeve with bolts, rivets, or the like, or any other mechanism or material capable of coupling the first and second pigtail catheters 100A1, 100A2 to one another. In some embodiments, instead of having a device to couple the first and second pigtail catheters 100A1, 100A2 to one another, they may be coupled together via a welding technique such as ultrasonic welding. The coupling device 190A should be configured to couple the first and second pigtail catheters 100A1, 100A2 to one another so that the first and second pigtail catheters 100A1, 100A2 are maintained in a fixed orientation. Thus, the first and second pigtail catheters 100A1, 100A2 should not be capable of moving axially relative to one another, moving towards or away from one another, or moving rotationally relative to one another.

Figure 3B:
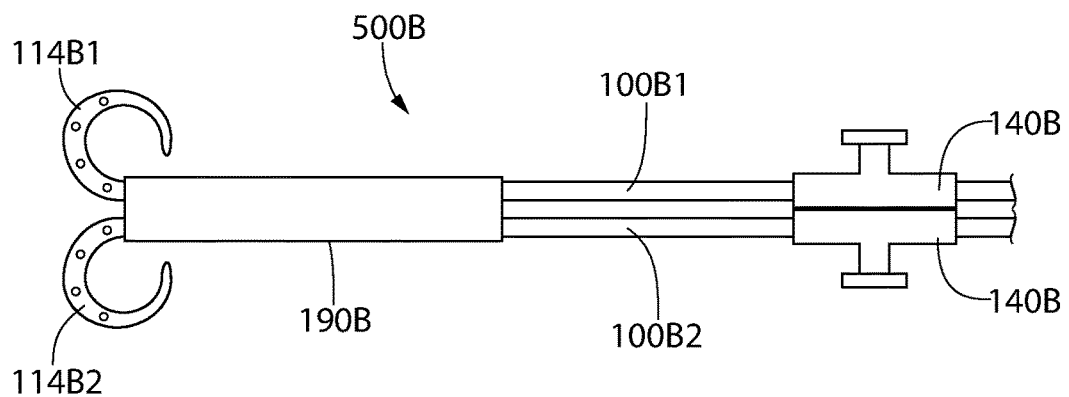
FIG. 3B is a side view of a catheter device that includes a first pigtail catheter and a second pigtail catheter that are coupled together in accordance with another embodiment of the present invention.

Referring briefly to FIG. 3B, a coupling device 190B in accordance with an alternative embodiment is shown. FIG. 3B illustrates that the coupling device 190B may comprise a sleeve that surrounds a portion of the body portion of the first and second pigtail catheters 100B1, 100B2. The sleeve 190B may be coupled to the first and second pigtail catheters 100B1, 100B2 using adhesive, bolts, screws, rivets, mechanical interaction, friction, or the like.

Referring again to FIG. 3A, when the first and second pigtail catheters 100A1, 100A2 are coupled together, the first longitudinal axis B-B of the first pigtail catheter 100A1 is parallel to the second longitudinal axis C-C of the second pigtail catheter 100A2 (and the first and second longitudinal axes B-B, C-C are both parallel to the longitudinal axis Z-Z of the catheter device 500A). Moreover, the tail portion 114A1 of the first pigtail catheter 100A1 curls away from the first longitudinal axis A-A in a first direction and the tail portion 114A2 of the second pigtail catheter 100A2 curls away from the second longitudinal axis B-B in a second direction that is different from the first direction. Specifically, in the exemplified embodiment the second direction is opposite the first direction. Thus, stated another way, the first tail portion 114A1 extends from the longitudinal axis Z-Z of the catheter device 500A in a direction that is opposite the direction that the second tail portion 114A2 extends from the longitudinal axis Z-Z of the catheter device 500A. The first and second tail portions 114A1, 114A2 extend in directions that are 180° from one another. The coupling device 190A serves to ensure that the opposing extension/curl direction of the first and second tail portions 114A1, 114A2 is maintained throughout a medical procedure.

Of course, it may be possible to couple the first and second pigtail catheters 100A1, 100A2 together with the first and second longitudinal axes A-A, B-B being non-parallel, which would also affect the relative directions with which the first and second tail portions 114A1, 114A2 extend from their respective longitudinal axes A-A, B-B and the longitudinal axis Z-Z of the catheter device 500A. Each of the first and second pigtail catheters 100A1, 100A2 can be coupled to one or both of an irrigation source and a suction source as described above with reference to FIGS. 1A and 1B and described below with reference to FIGS. 25-28.

Moreover, although in the exemplified embodiment the coupling device 190A couples the body portions 110A1, 110A2 of the first and second pigtail catheters 100A1, 100A2 together, this is not required in all embodiments.

Specifically, in the exemplified embodiment, each of the first and second pigtail catheters 100A1, 100A2 has one of the valves 140A coupled thereto. In some embodiments, the valves 140A may be coupled to one another rather than the pigtail catheters 100A1, 100A2 being directly coupled to one another. In one such embodiment, two valves 140A may form a single unit or integral/monolithic structure. Coupling of the valves 140A to one another will, in effect, also couple the first and second pigtail catheters 100A1, 100A2 to one another when the valves 140A or monolithic valve structure is coupled to the first and second pigtail catheters 100A1, 100A2. With the valves 140A fixed relative to each other and the first and second pigtail catheters 100A1, 100A2 fixed to the valves 140A, the relative orientation of the first and second pigtail catheters 100A1, 100A2 can be fixed. In some embodiments, indicia or markings may be present on the first and second pigtail catheters 100A1, 100A2 and/or on the valves 140A or other structures to ensure that the pigtail catheters 100A1, 100A2 are properly oriented relative to each other. In embodiments where the first and second pigtail catheters 100A1, 100A2 may be inserted into the patient without the valves 140A attached to the first and second pigtail catheters 100A1, 100A2, some other type of orienting device (i.e., coupling device 190A) can be used. For example, the first and second pigtail catheters 100A1, 100A2 can be fixed to each other by an adhesive, a clip, a clamp, or some other coupling device.

Because the first and second pigtail catheters 100A1, 100A2 are coupled together, they can both be inserted into a patient simultaneously through a single incision. Both of the first and second pigtail catheters 100A1, 100A2 can be used to evacuate the body cavity or one can be used to irrigate and the other to evacuate. By providing two catheters through a single incision, the risk of infection and other risks associated with piercing the body cavity can be reduced.

Referring to FIGS. 4-8, of a body cavity irrigation and drainage system 10 (hereinafter "the system") is illustrated in accordance with an embodiment of the present invention. The system 10 generally comprises a first pigtail catheter 20, a second pigtail catheter 30, and a sheath 40 surrounding the first and second pigtail catheters 20, 30. The first and second pigtail catheters 20, 30 may be formed as a part of a catheter device, such as the catheter device 500A, 500B described above with reference to FIGS. 3A and 3B. Thus, the system 10 may comprise the catheter device 500A, 500B and the sheath 40 in some embodiments.

The system 10 may also comprise valves 60 coupled to the first and second pigtail catheters 20, 30, suction and/or irrigation sources (not shown in FIGS. 4-8), and conduits or tubes 50 extending from the valves 60 to the suction and/or irrigation sources. Of course, the system 10 could include only the first and second pigtail catheters 20, 30 and the sheath 40 in some embodiments, although the coupling to the suction/irrigation sources may be needed to perform a medical procedure.

The first and second pigtail catheters 20, 30 are identical to the pigtail catheter 100 described above with reference to FIGS. 1A and 1B and thus a detailed description of the first and second pigtail catheters 20, 30 will not be provided here in the interest of brevity. The sheath 40 extends from a first end 41 to a second end 42 and comprises an outer surface 43 and an inner surface 44 that defines a cavity 45. The first end 41 of the sheath 40 is the end that is intended to be inserted into a body cavity of a patient through an incision. In some embodiments, the sheath 40 may not be inserted entirely into the body cavity of the patient such that the second end 42 of the sheath 40 and a portion of the sheath 40 adjacent to the second end may always be located external to the body cavity/skin of the patient.

The cavity 45 is open at each of the first and second ends 41, 42 of the sheath 40 such that the cavity 45 forms a passageway through the sheath 40 from the first end 41 to the second end 42. The sheath 40 extends along a longitudinal axis D-D from the first end 41 to the second end 42. The sheath 40 comprises a first pull tab 46 protruding from the outer surface 43 on a first side of the longitudinal axis D-D and a second pull tab 47 protruding from the outer surface 43 on a second side of the longitudinal axis D-D that is opposite the first side of the longitudinal axis D-D. Thus, the first and second pull tabs 46, 47 extend from the outer surface 43 of the sheath 40 in opposite directions that are 180° apart in the exemplified embodiment. As will be explained further below, the pull tabs 46, 47 facilitate tearing of the sheath 40 so that it can be removed from a body cavity of a patient while the first and second pigtail catheters 20, 30 remain in the body cavity of the patient.

As shown, the first and second pigtail catheters 20, 30 are located in the cavity 45 of the sheath 40 such that the sheath 40 surrounds the first and second pigtail catheters 20, 30. In the exemplified embodiment, the distal tips of the first and second pigtail catheters 20, 30 protrude/extend from the second end 42 of the sheath 40, but in other embodiments this may not be the case and the distal ends of the first and second pigtail catheters 20, 30 may be located within the cavity 45 of the sheath 40. The first and second pigtail catheters 20, 30 may be part of a catheter device like the catheter device 500A of FIG. 3A and in that regard the first and second pigtail catheters 20, 30 may be coupled together as described with regard to that embodiment. Specifically, as shown in FIG. 7, there may be a coupling device 90 coupling the first and second pigtail catheters 20, 30 to one another to prevent relative movement therebetween.

In the embodiment of FIGS. 4-8, the sheath 40 acts to maintain the first and second pigtail catheters 20, 30 in the first state (i.e., the straightened state). That is, the first pigtail catheter 20 comprises a first tail portion 21 and the second pigtail catheter 30 comprises a second tail portion 31. The sheath 40 forces the first and second tail portions 21, 31 of the first and second pigtail catheters 20, 30 to remain straight and elongated along the longitudinal axes of the first and second pigtail catheters 20, 30. The first and second tail portions 21, 31 of the first and second pigtail catheters 20, 30 are curled in their natural state, and thus they will attempt to curl when within the sheath 40. However, the tail portions 21, 31 will simply abut against the inner surface 44 of the sheath 40, which will prevent them from fully curling. In that regard, in FIGS. 4-8 the first and second pigtail catheters 20, 30 do not have cannulas in them for purposes of straightening them as described above with reference to FIG. 3 because the sheath 40 keeps the first and second pigtail catheters 20, 30 in the substantially straight condition for insertion into the patient. In other embodiments, the first and second pigtail catheters 20, 30 may have cannulas in them even when they are positioned within the sheath 40 (described in more detail below with reference to FIG. 14).

As best seen in FIGS. 6-8, in the exemplified embodiment the first and second pigtail catheters 20, 30 are round and are of such diameters that they touch, or are very close to touching, the inside walls of cavity 45. In other embodiments, the first and second pigtail catheters 20, 30 fit tightly inside the cavity 45 of the sheath 40 such that the first and second pigtail catheters 20, 30 are slightly deformed while disposed therein. In still other embodiments, the first and second pigtail catheters 20, 30 fit loosely in the cavity 45. In some embodiments, the first and second pigtail catheters 20, 30 have a cross-sectional shape other than a circle, such as, for example, a circular segment, an oval, a semi-circle, or a triangle.

FIG. 7 is a partial sectional view along section line VII-VII in FIG. 6 and shows the first and second pigtail catheters 20, 30 inside the cavity 45 of the sheath 40. For clarity, the first and second pigtail catheters 20, 30 are shown not touching each other in FIG. 7. However, it is noted that the first and second pigtail catheters 20, 30 can touch each other while in sheath 40. It is also noted that this example has valves 60 attached to the first and second pigtail catheters 20, 30 prior to insertion into the patient. Other embodiments do not attach the valves 60 until after the sheath 40 is removed. The embodiment of FIG. 7 does not have cannulas inside the first and second pigtail catheters 20, 30. However, other embodiments have cannulas inside the first and second pigtail catheters 20, 30 in this state.

FIG. 9-13 illustrate an installation of the system 10 or a part thereof into a body cavity of a patient. FIG. 9 shows a portion of the sheath 40 with the first and second pigtail catheters 20, 30 (or the catheter device 500) located therein inserted partially through skin S of a patient such that part of the sheath 40 is inside ("I") the patient and part of the sheath 40 is outside ("O") the patient. Specifically, as noted above in the description of the Seldinger technique, the first step in this process which is not shown here would involve inserting a guidewire through a needle that is penetrating the skin S of the patient. The needle would then be removed and a dilater would be passed over the guidewire to expand the opening through the skin S, which could be enhanced with the use of an incision instrument. Next, the dilater would be removed and the sheath 40 with the first and second pigtail catheters 20, 30 therein would be passed over the guidewire and inserted inside I of the patient (i.e., into a body cavity of the patient, such as, for example without limitation, the pleural space). The guidewire could then be removed, which would result in what is shown in FIG. 9, although the guidewire may remain until the sheath 40 and catheters 20, 30 are in the desired position within the body cavity (see FIG. 10 and description below).

In some embodiments, the sheath 40 may have an outside diameter of more than 20 Fr, and in some cases more than 32 Fr. With a sheath of this size, it is sometimes desirable or necessary to use one or more dilaters to gradually increase the size of the opening in the patient so that the sheath 40 can be inserted. If dilaters are needed, the dilation process takes place prior to the state shown in FIG. 9 as discussed above.

FIG. 10 shows the system 10 (more specifically, the sheath 40 and the first and second pigtail catheters 20, 30 disposed therein) inserted farther into the patient than in FIG. 9. At this position the system 10 is fully inserted in the body cavity within the interior I of the patient and the sheath 40 can be removed to deploy the first and second pigtail catheters 20, 30 within the body cavity. As discussed below, such deployment automatically causes the first and second pigtail catheters 20, 30 to transition from the first straightened state to the second curled state (compare FIG. 11 with FIG. 12). In FIGS. 9 and 10, the first and second pigtail catheters 20, 30 are in the first straightened state because they are positioned within the sheath 40 and the sheath forces them into this straightened state.

As can be seen, as the first and second pigtail catheters 20, 30 are inserted through an incision in the skin S into the interior of the patient while located within the sheath 40, the first and second pigtail catheters 20, 30 are inserted into the same incision simultaneously. Thus, using the system 10 described herein, the first and second pigtail catheters 20, 30 can be inserted through a single incision at the same time for positioning within a body cavity for irrigation and/or drainage. Although FIGS. 9 and 10 illustrate the system 10 that utilizes the sheath, in other embodiments the catheter device 500A, 500B of FIGS. 3A and 3B could be inserted into the single incision at the same time, although when using the catheter device 500A, 500B without the sheath 40, cannulas would need to be positioned within the first and second pigtail catheters 100A1, 100A2 during the insertion process to maintain the first and second pigtail catheters 100A1, 100A2 in the first (straightened) state. Needless to say, the insertion of two pigtail catheters into a single incision in the skin S of a patient can be accomplished with the two pigtail catheters disposed within a sheath or not.

Referring to FIG. 10 and to the system 10, after the sheath 40 and the first and second pigtail catheters 20, 30 are inserted through the incision in the skin S and into the inside I of the patient, the sheath 40 must be removed so that the first and second pigtail catheters 20, 30 can be deployed and altered into the second (curled) state. In the exemplified embodiment, the sheath 40 is configured to be separated or torn into a first part 48 and a second part 49 to facilitate the removal of the sheath 40 from the inside I of the patient while leaving the first and second pigtail catheters 20, 30 inside I of the patient. In the exemplified embodiment, separating or otherwise tearing or breaking the sheath 40 is accomplished by a user simultaneously pulling the pull tabs 46, 47 in opposite directions as shown by the arrows A. In some embodiments, perforations or some other weakened areas 99 can be provided on the sheath 40 to direct the separation of sheath 200 into the first and second parts 48, 49 upon the user pulling on the pull tabs 46, 47.

In the exemplified embodiment, the sheath 40 is configured to be torn in a direction from the second end 42 towards the first end 41. The sheath 40 does not need to be torn along its entire length, although it could be in some embodiments. Rather, the sheath 40 could be torn partially along its length a sufficient distance to enable a user/operator to remove the sheath 40 from the body cavity through the incision.

While this example shows the sheath 40 being separated into two parts, in other examples the sheath 40 may be separated into three or more parts. Furthermore, in the exemplified embodiment the sheath 40 is torn along a line that is parallel to its axis. In other embodiments, the sheath 40 may be torn in a spiral-like pattern. In still other embodiments, the sheath 40 may comprise many axial sections such that each axial section can be separated/torn from the remainder of the sheath 40 one at a time. Thus, there are many different ways that the sheath 40 can be torn for removal. As the sheath 40 is being torn along the pre-weakened line 99 or otherwise, a user will pull the sheath 40 out of the inside I of the patient through the incision by pulling the sheath 40 axially away from the skin S (see FIGS. 11 and 12). This combination of tearing and pulling on the sheath 40 will cause the sheath 40 to be pulled entirely out of the inside I of the patient, leaving the first and second pigtail catheters 20, 30 within the body cavity in the inside I of the patient (see FIG. 13).

While the pull tabs 46, 47 are shown in this example as the structure that facilitates the tearing of the sheath 40, it is noted that other means of separating the sheath 40 can be employed, such as, for example, pull rings molded into the sheath 40 or strings that can be pulled to tear the sheath 40 into two or more parts. Alternatively, a user/operator could use a sharp blade to cut the sheath 40 to facilitate its removal. The separation of the sheath 40 can be necessitated by structure such as the valves 60 preventing the sheath 40 from simply sliding to the right in FIGS. 9-13. Even in embodiments where there is no structure preventing the sheath 40 from sliding to the right in FIGS. 9-13, it can be necessary to hold the first and second pigtail catheters 20, 30 in their current position while removing the sheath 40 so that the first and second pigtail catheters 20, 30 are not pulled out of the patient along with the sheath 40. This might be most easily accomplished by separating the sheath 40 into two or more pieces as described herein.

As noted above, FIG. 12 shows the continued separation of the sheath 40 into parts 48, 49 as the sheath 40 is pulled axially in the direction of arrow C. As the sheath 40 is pulled in the direction of arrow C, the first and second pigtail catheters 20, 30 begin to exit the sheath 40 and return to their naturally curved configurations. Specifically, as noted above the sheath 40 alone may be maintaining the first and second pigtail catheters 20, 30 in the first straightened state. Thus, as the sheath 40 is removed from the patient through the incision in the skin S, the tail ends 21, 31 of the first and second pigtail catheters 20, 30 become removed from the cavity of the sheath 40. As the first and second tail ends 21, 31 of the first and second pigtail catheters 20, 30 become removed from the cavity of the sheath 40, the first and second tail ends 21, 31 of the first and second pigtail catheters 20, 30 will automatically return to the second curled or curved state, which is the natural state of the first and second pigtail catheters 20, 30.

FIG. 13 shows the sheath 40 completely removed from the inside I of the patient so that the first and second pigtail catheters 20, 30 are no longer housed within the sheath 40. As such, the first and second pigtail catheters 20, 30 are installed in the body cavity of the patient and ready for use. In embodiments where the first and second pigtail catheters 20, 30 do not have a naturally curved configuration, whatever method is used to curl the ends of the first and second pigtail catheters 20, 30 would be employed at this point. As shown, the first and second tail portions 21, 31 of the first and second pigtail catheters 20, 30 curl in opposite directions once installed, as described above with regard to FIGS. 3A and 3B. Furthermore, the first and second pigtail catheters 20, 30 may be coupled together with a coupling device even when the sheath 40 is removed. The first and second pigtail catheters 20, 30 may also at this point be operably coupled to an irrigation and/or suction/vacuum source to perform an irrigation and/or suction operation, as described in more detail below with reference to FIGS. 25-28.

Figure 14:
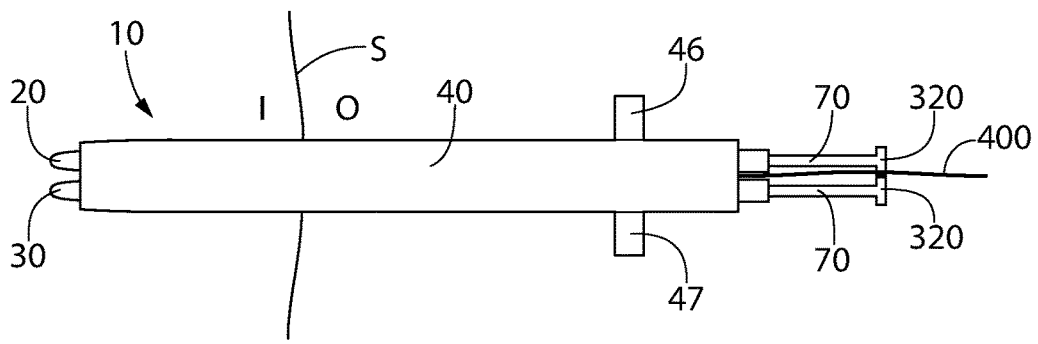
FIG. 14 is a schematic side view of the system of FIG. 4 inserted into a body cavity of a patient, wherein the system also includes cannulas disposed within the first and second pigtail catheters.
Figure 15:
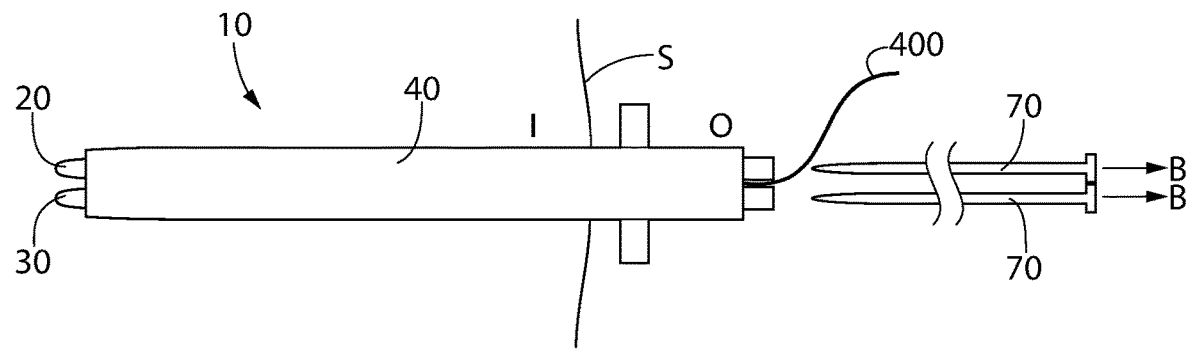
FIG. 15 is the schematic side view of FIG. 14 illustrating the cannulas being removed from the first and second pigtail catheters.
Figure 16:
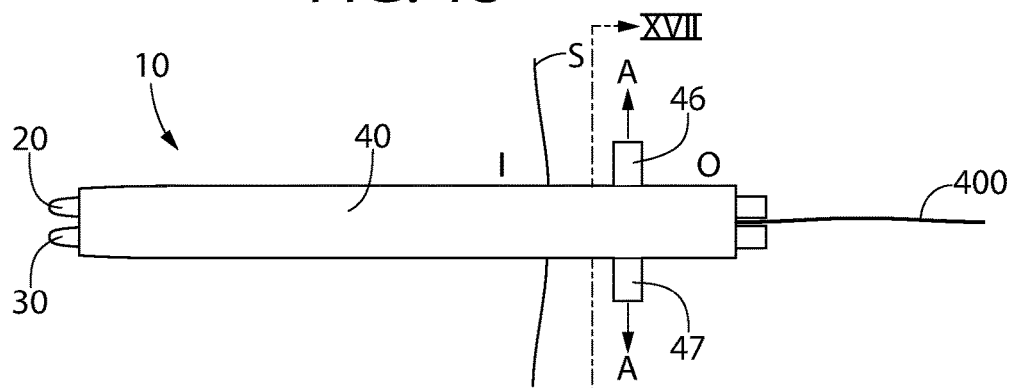
FIG. 16 is the schematic side view of FIG. 14 with the cannulas having been removed.
Figure 17:
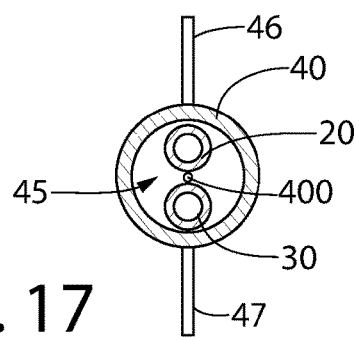
FIG. 17 is a cross-sectional view taken along line XVII-XVII of FIG. 16

As discussed above, some embodiments may use a cannula in one or more of the first and second pigtail catheters 20, 30 to keep the first and second pigtail catheters 20, 30 straight during insertion into the patient. FIGS. 14-16 show an example of the system 10 that includes cannulas 70.

FIG. 14 shows the system 10 whereby the sheath 40 with the first and second pigtail catheters 20, 30 disposed therein are inserted partially through the skin S of a patient such that part of the sheath 40 and the first and second pigtail catheters 20, 30 are inside ("I") the patient and part of the sheath 40 and the first and second pigtail catheters 20, 30 are outside ("O") the patient. FIG. 14 is very similar to FIG. 9 described above, except that in this embodiment there are cannulas 70 positioned within the first and second pigtail catheters 20, 30 to force them into the first (straightened) state. As described above, in some embodiments the cannulas 70 may be inserted into the first and second pigtail catheters 20, 30 to straighten them before the first and second pigtail catheters 20, 30 are placed inside of the sheath 40. In other embodiments, the cannulas 70 may not be used.

Referring to FIG. 15, the system 10 is illustrated fully inserted into the body cavity in the inside I of the patient. In this embodiment, once the system 10 is fully inserted, the cannulas are removed by withdrawing them from first and second pigtail catheters 20, 30 in the direction of arrows B. However, in other embodiments, the cannulas 70 may remain within the first and second pigtail catheters 20, 30 while the sheath 40 is being removed as described above with reference to FIGS. 10-13 in order to maintain the straight state of the first and second pigtail catheters 20, 30 during the removal of the sheath 40. In such embodiments, after the sheath 40 has been removed, the cannulas 70 can be removed from the first and second pigtail catheters 20, 30 to enable them to transition into their natural curled/curved state.

Referring to FIG. 16, the system 10 is illustrated with the cannulas 70 removed from the first and second pigtail catheters 20, 30. The next step is to remove the sheath 40, which may occur in the same fashion described above and shown in FIGS. 11 and 12, or in some other fashion.

In FIGS. 14-17, a guidewire 400 is also illustrated, the guidewire 400 and its purpose having been described above. As discussed, the guidewire 400 is passed through the incision in the skin S and then used to guide the first and second pigtail catheters 20, 30 and the sheath 40 through the incision in the skin and into the body cavity in the inside I of the patient. Thus, the guidewire 400 is used to guide the components of the system 10 to the proper location in the patient. In some embodiments, the guidewire 400 is inserted into the patient first and located with the help of imaging. After the guidewire 400 is properly located, the sheath 40 can be slid over the guidewire 400 to guide the sheath 40 and the first and second pigtail catheters 20, 30 to the desired location. In some embodiments, the guidewire 400 is simply threaded through an open space in the cavity 45 of the sheath 40. In other embodiments, a special passageway is formed in or on the sheath 40 through which the guidewire 400 is passed. Such a special passageway can help prevent the guidewire 400 from mistakenly entering an aperture 130 of one of the first and second pigtail catheters 20, 30.

The embodiments of FIGS. 9-17 use the sheath 40 to aid the insertion of the first and second pigtail catheters 20, 30 into the body of the patient. Other embodiments may not use a sheath. The sheath 40 may be a one-time use disposable component. Thus, the sheath 40 can be torn/ripped/cut as described herein and then discarded in some embodiments.

Figure 18:
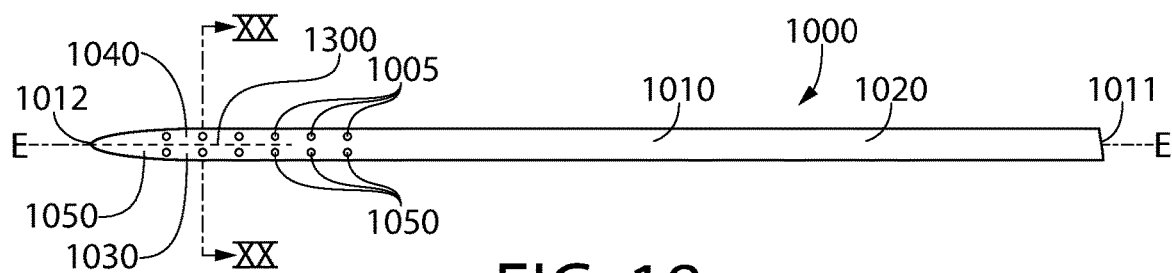
FIG. 18 is a side view of a body cavity irrigation and drainage device in accordance with another embodiment of the present invention.
Figure 19:
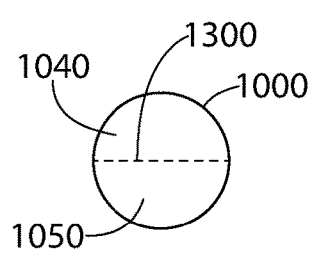
FIG. 19 is an end view of the device of FIG. 18.
Figure 20:
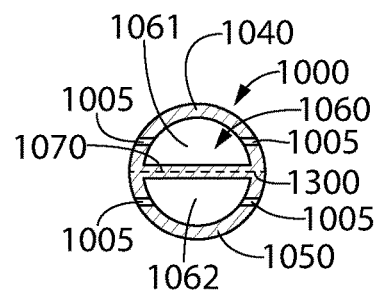
FIG. 20 is a sectional view along section line XX-XX in FIG. 18.

FIGS. 18-24 show examples of the invention that do not use a sheath. Referring first to FIGS. 18-20, a catheter device 1000 is illustrated in accordance with an embodiment of the present invention. The catheter device 1000 comprises a body 1010 that extends from a proximal end 1011 to a distal end 1012 along a longitudinal axis E-E. The body 1010 is formed as a single, unitary, integral, monolithic structure. In one embodiment, the catheter device 1000 may be formed as one unit during manufacturing by way of, for example, extruding. In other examples, two pigtail catheters may be formed during manufacturing by way of, for example, extruding, and then the two pigtail catheters may be bonded together by welding, adhesive, or other method to form the catheter device 1000.

The catheter device 1000 comprises a proximal portion 1020 and a distal portion 1030. There are a plurality of apertures 1005 in the distal portion 1030 having a similar structure and function to the apertures described above with regard to the previously described embodiments. As will be discussed in more detail below with reference to FIGS. 23 and 24, the distal portion 1030 is alterable between a first state in which the distal portion 1030 is elongated along the longitudinal axis E-E and a second state in which the distal portion 1030 is separated into a first tail portion 1040 and a second tail portion 1050 that extend from the longitudinal axis E-E in opposite directions.

The catheter device 1000 comprises a cavity 1060 that extends internally within the catheter device 1000 from the proximal end 1011 to the distal end 1012. Furthermore, the catheter device 1000 comprises an internal wall 1070 located within the cavity 1060 that divides the cavity 1060 into a first flow channel 1061 and a second flow channel 1062. The internal wall 1070 extends an entirety of the length of the cavity 1070, and thus the first and second flow channels 1061, 1062 are fluidly isolated from one another along the entire length of the cavity 1070. As a result, a fluid can be injected into a body cavity through one of the first and second flow channels 1061, 1062 while suction is applied to the body cavity through the other one of the first and second flow channels 1061, 1062.

In the exemplified embodiment, the catheter device 1000 also comprises a weakened section 1300 that extends axially along the distal portion 1030 of the body 1010. The weakened section 1300 could be formed by a series of spaced apart perforations, a thinned wall, a pre-cut region, or the like. The catheter device 1000 is configured to tear along the weakened section 1300 to alter the body 1010 from the first state (FIGS. 18 and 23) to the second state (FIG. 24), as described further herein. The weakened section 1300 is formed into the body 1010 along the distal portion 1030 thereof and it is formed into the internal wall 1070. Thus, as the body 1010 is torn along the weakened section 1300, the internal wall 1070 also tears along the weakened section to maintain the two distinct first and second flow channels 1061, 1062.

In the exemplified embodiment, the weakened section 1300 is planar. In other embodiments, the weakened section 1300 may not be planar. Still other examples can have three or more pigtail sections with weakened sections between each pigtail section.

FIG. 20 is a sectional view taken along section line XX-XX in FIG. 18 and shows the first and second flow channels 1061, 1062 that run the length of catheter device 1000. These are analogous to the channels that run through pigtail catheters 100 in the embodiments shown in previous embodiments. The weakened section 1300 is shown in FIG. 20 as running between the first and second flow channels 1061, 1062 and separating the internal wall 1070 that borderers both of the first and second flow channels 1061, 1062. Upon separation of the first and second tail portions 1040, 1050 from one another, the internal wall 1070 splits to provide separate walls for each of the first and second flow channels 1061, 1062.

Figure 21:
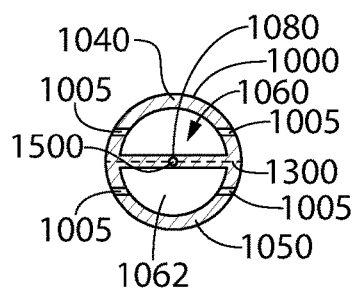
FIG. 21 is a first alternate sectional view along section line XX-XX in FIG. 18.

FIG. 21 is similar to FIG. 20 except that a passageway 1080 is provided in the internal wall 1070. The passageway 1050 provides a path for a guide wire 1500 (shown in FIG. 22) that is used to guide the catheter device 1000 to the proper location in the patient. In some embodiments, guidewire 1500 is inserted in the patient first and located with the help of imaging. After the guidewire 1500 is properly located, the catheter device 1000 can be slid over the guidewire 1500 to guide the catheter device 1000 the desired location. In the embodiment shown in FIGS. 18-21, the catheter device 1000 is made of a material sufficiently rigid to penetrate the patient without further support.

Figure 22:
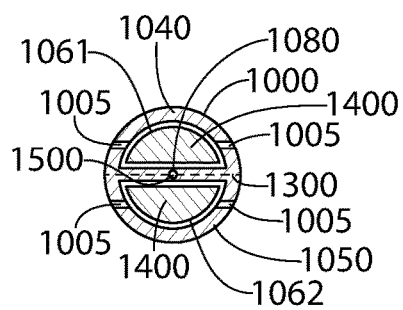
FIG. 22 is a second alternate sectional view along section line XX-XX in FIG. 18.

FIG. 22 is similar to FIG. 21 except that a cannula 1400 is positioned in each of the first and second flow channels 1061, 1062. The cannulas 1400 can be formed from a rigid material that supports the catheter device 1000 to maintain a straight state. After the catheter device 1000 is properly located in the patient, the cannulas 1400 may be removed. The cannulas 1400 may not be required in some embodiments. In some embodiments, removal of cannulas 300 will allow the first and second tail portions 1040, 1050 of the body 1010 to separate from each due only to the force of the pre-stressed material returning to a curved state. Specifically, if the pre-weakened section 1300 is sufficiently weakened and the natural curve force of the first and second tail portions 1040, 1050 sufficiently strong, it is possible that removing the cannulas 1400 may cause the catheter device 1000 to automatically transition from the first straight state to the second curled/curved state. In other embodiments, external force is applied to separate the first and second tail portions 1040, 1050 of the body 1010 from each other.

Figure 23:
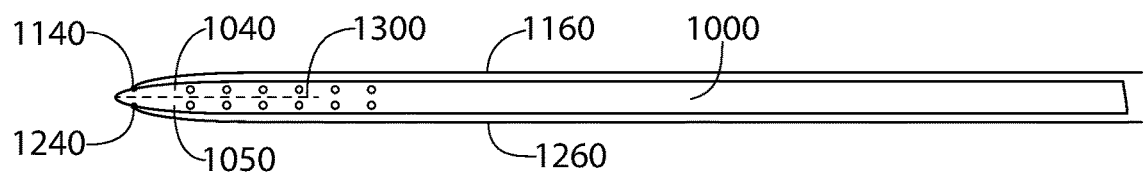
FIG. 23 is a side view of the device of FIG. 18 with pull strings coupled to a distal end thereof, the device being in a first state whereby a distal end of the device is straight.
Figure 24:
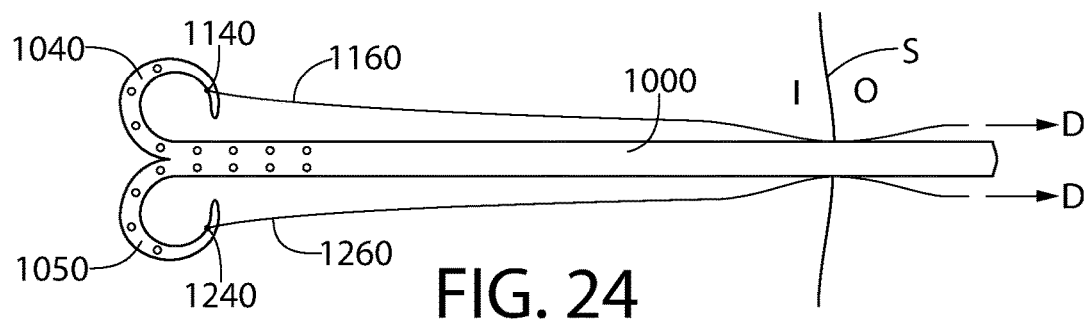
FIG. 24 is a side view of device of FIG. 23 after the pull strings have been pulled to alter the device into a second state wherein the distal end of the device is separated into first and second tail sections that curl in opposite directions.

Referring to FIGS. 23 and 24, an embodiment that includes pull strings to facilitate the transitioning of the catheter device 1000 from the straightened state (FIG. 23) to the curled state (FIG. 24) will be described. A first pull string 1160 is attached to the catheter device 1000 near the end of the first tail portion 1040 at a first connection point 1140 and a second pull string 1260 is attached to the catheter device 1000 near the end of the second tail portion 1050 at a second connection point 1240. After the catheter device 1000 is in the proper location in the patient, and after the cannula 1400 is removed (if used), the first and second pull strings 1160, 1260 are pulled in the direction of arrow D to separate the first tail portion 1040 from the second tail portion 1050.

As the first and second tail portions 1040, 1050 separate, so too does the internal wall 1070 separate. Thus, each of the first and second tail portions 1040, 1050 comprises a portion of the internal wall 1070 once separated so that the first and second flow channels 1040, 1050 remain intact. Once separated as shown in FIG. 24, the first tail portion 1040 comprises a distal portion of the first flow channel 1061 and the second tail portion 1050 comprises a distal portion of the second flow channel 1062. Of course, the use of the first and second pull strings 1160, 1260 is only one technique for separating the catheter device 1000 as described and shown, and other structures, techniques, or the like could be used in other embodiments to achieve this same result.

Referring to FIGS. 25-28, the catheter device 500A is illustrated in use coupled to an irrigation and/or suction source. It should be appreciated that the catheter device 500A could be the one depicted and described with reference to FIGS. 3A and 3B, a part of the system 10 depicted and described with reference to FIGS. 4-17, or the catheter device 1000 depicted and described with reference to FIGS. 18-24. Any of these systems or devices can be coupled to an irrigation source and/or a suction source for operation thereof. Thus, the operation is the same regardless of which device/system is used and it should be appreciated that the description below with reference to FIGS. 25-28 could be applied to any of the systems, devices, apparatuses, or the like described above.

Figure 25:
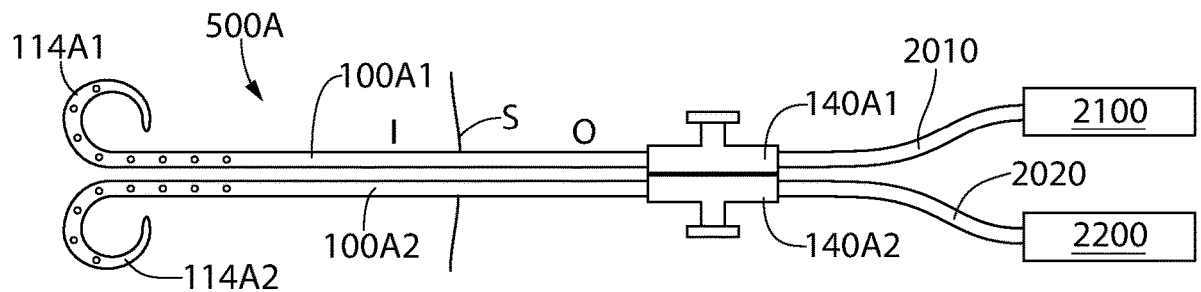
FIG. 25 is a side view of the system of FIG. 13 in the body cavity of the patient whereby the first and second pigtail catheters are operably coupled to an irrigation source and a suction source.

Referring first to FIG. 25 the catheter device 500A comprising the first pigtail catheter 100A1 and the second pigtail catheter 100A2 is illustrated installed in a body cavity within the interior I of the patient. In the exemplified embodiment, a suction generator and irrigation machine 2100 is attached to the fist pigtail catheter 100A1 by way of a first valve 140A1 and tubing 2010. The suction generator and irrigation machine 2100 can generate suction for evacuation through the first pigtail catheter 100A1, and can also provide irrigation fluid to the first pigtail catheter 100A1 by way of the tubing 2010 and the first valve 140A1. In some embodiments, the suction generator and irrigation machine 2100 can alternate between evacuation and irrigation. Although in the exemplified embodiment the first pigtail catheter 100A1 is coupled to a single machine that is configured for both suction and irrigation, in other embodiments the first pigtail catheter 100A1 may be coupled to a suction source and to an irrigation source separately. In such embodiments, the valve 140A1 may be a three-way valve so that separate tubing may extend from the first pigtail catheter 100A1 to the suction source and to the irrigation source.

The second pigtail catheter 100A2 is coupled to a suction generator and irrigation machine 2200 by way of a second valve 140A2 and tubing 2020. In some embodiments, the first and second pigtail catheters 100A1, 100A2 may be coupled to the same suction generator and irrigation machine. In other embodiments, the first and second pigtail catheters 100A1, 100A2 may be coupled to the same suction source and separately to the same irrigation source. Thus, various permutations of this are possible so long as both of the first and second pigtail catheters 100A1, 100A2 are configured to apply suction to the body cavity and irrigate the body cavity, in some embodiments. In the exemplified embodiment, the suction generator and irrigation machine 2200 can generate suction for evacuation through the second pigtail catheter 100A2, and can also provide irrigation fluid to the second pigtail catheter 100A2 by way of tubing 2020 and valve 240A2. In some embodiments, the suction generator and irrigation machine 2200 can alternate between evacuation and irrigation. Although in the exemplified embodiment the second pigtail catheter 100A2 is coupled to a single machine that is configured for both suction and irrigation, in other embodiments the second pigtail catheter 100A2 may be coupled to a suction source and to an irrigation source separately. The suction source could be a pleur-evac and the irrigation source could be a fluid drip or intravenous drip, such as a saline drip, that operates via gravity, in some embodiments. In such embodiments, the valve 140A2 may be a three-way valve so that separate tubing may extend from the second pigtail catheter 100A2 to the suction source and to the irrigation source. Other embodiments provide a suction only or irrigation only machine attached to either one or both of the first and second pigtail catheters 100A1, 100A2. The first and second valves 140A1, 140A2 can be valves that are infinitely or step adjustable to allow partial flow through the valve in order to regulate the level of irrigation and evacuation.

Figure 26:
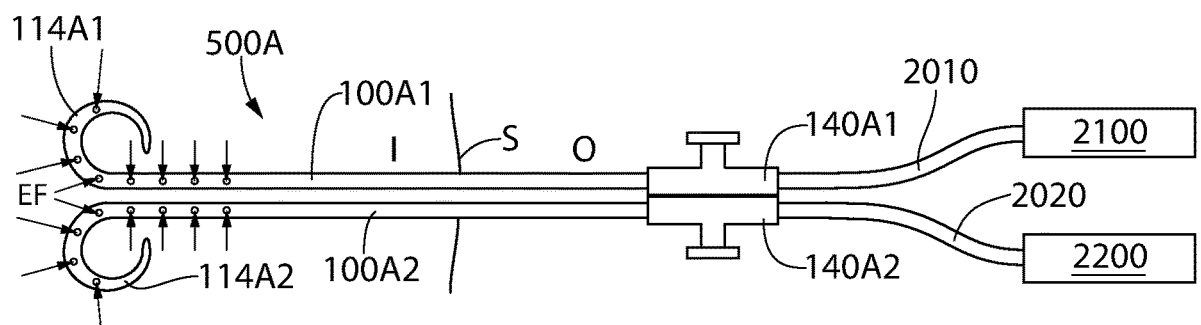
FIG. 26 is a side view of the system shown in FIG. 25 wherein both of the pigtail catheters are applying suction to the body cavity.

FIG. 26 shows the catheter device 500A of FIG. 25 operating to provide suction to both of the first and second pigtail catheters 100A1, 100A2 to remove evacuation fluid EF from the patient. In this state, one or both of the first and second valves 140A1, 140A2 can be adjusted to provide the level of suction desired for the required evacuation.

Figure 27:
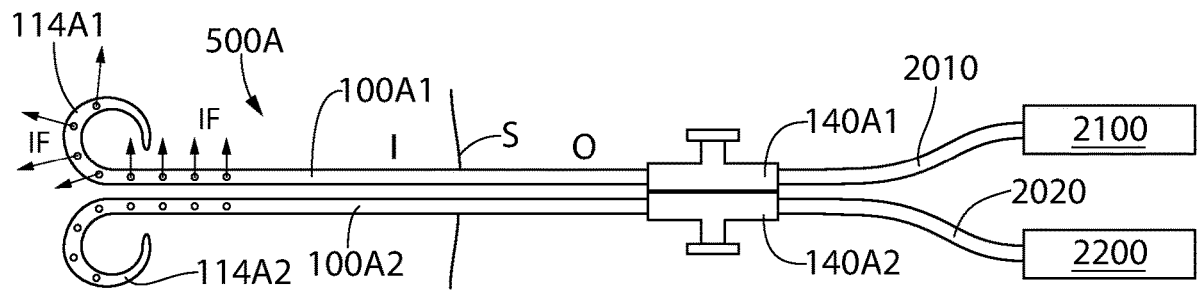
FIG. 27 is a side view of the system shown in FIG. 25 wherein one of the pigtail catheters is irrigating the body cavity.

FIG. 27 shows the catheter device 500A of FIG. 25 operating to provide irrigation to only the first pigtail catheter 100A1 to inject irrigation fluid IF from the first pigtail catheter 100A1 into the patient. In this state, the first valve 140A1 can be adjusted to provide the level of fluid desired for the required irrigation.

Figure 28:
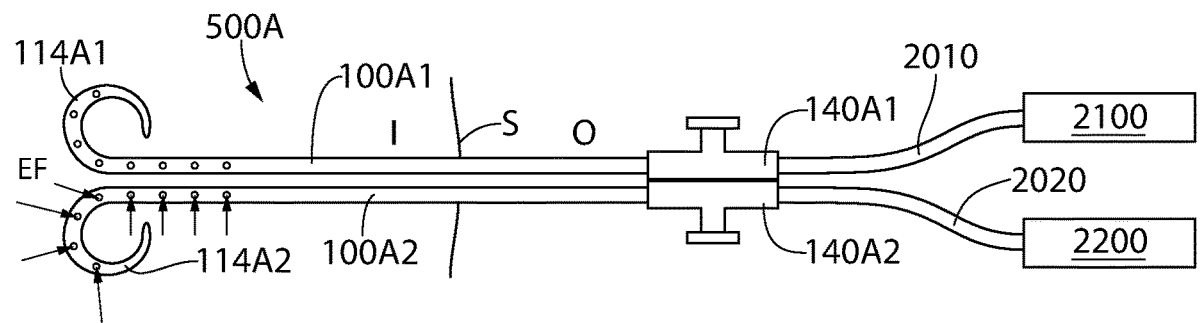
FIG. 28 is a side view of the system shown in FIG. 25 wherein one of the pigtail catheters is applying suction to the body cavity.

FIG. 28 shows the catheter device 500A of FIG. 25 operating to provide suction to only the second pigtail catheter 100A2 to remove evacuation fluid EF from the patient. In this state, the second valve 140A2 can be adjusted to provide the level of suction desired for the required evacuation.

Any combination of the states shown in FIGS. 25-28 can be used to provide any combination of irrigation, evacuation, and no flow/closed in each of the first and second pigtail catheters 100A1, 100A2. For example, in some embodiments the first pigtail catheter 100A1 can be injecting a fluid into the patient for irrigation while simultaneously the second pigtail catheter 100A2 is evacuating fluid from the patient via suction, and vice versa. In some embodiments, both of the first and second pigtail catheters 100A1, 100A2 may be irrigating the body cavity, in some embodiments both of the first and second pigtail catheters 100A1, 100A2 may be evacuating the body cavity via suction, etc.

Figure 29:
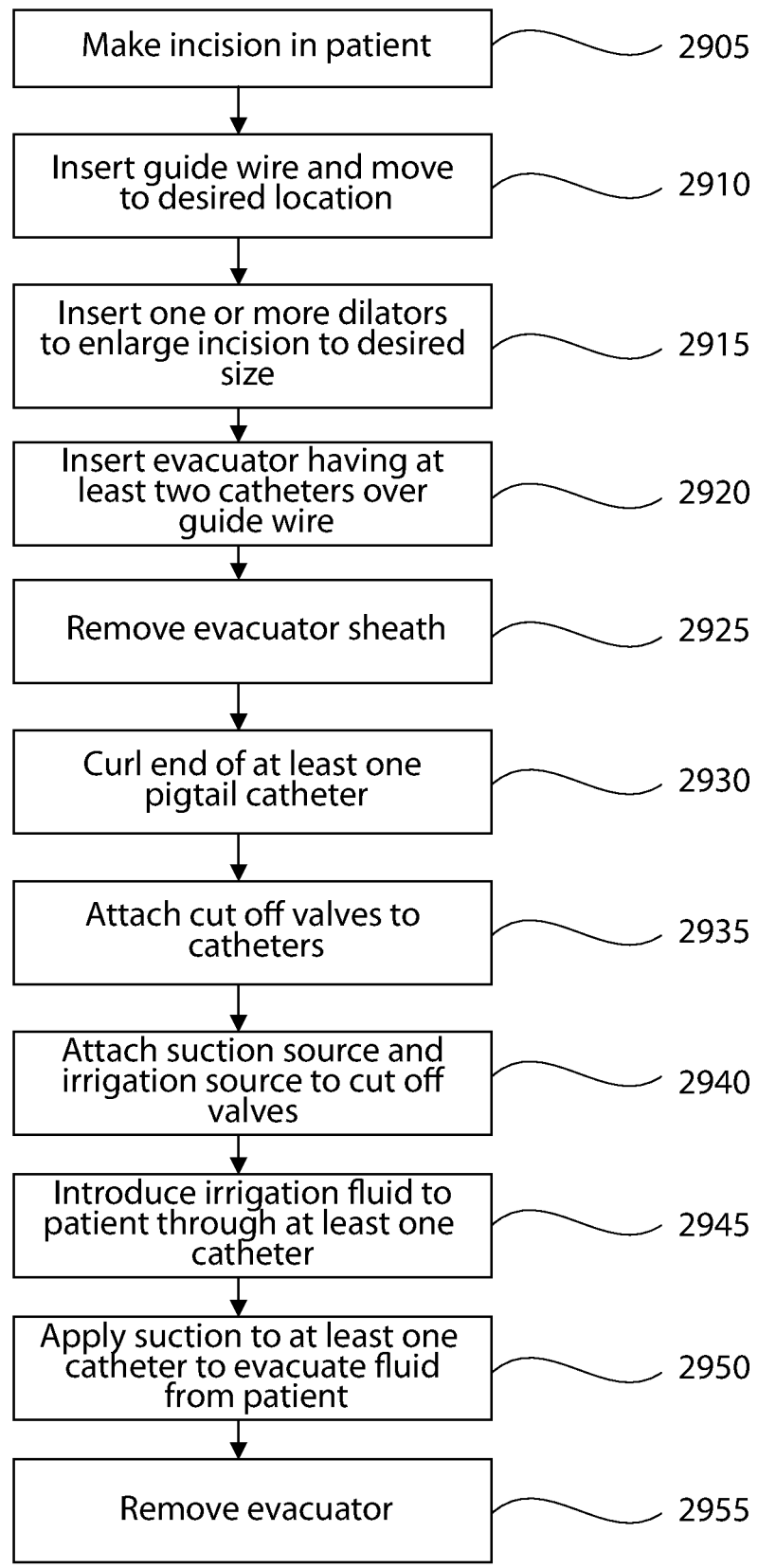
FIG. 29 is a flow chart associated with a method of irrigating and draining a body cavity in accordance with an embodiment of the present invention.
Figure 30:
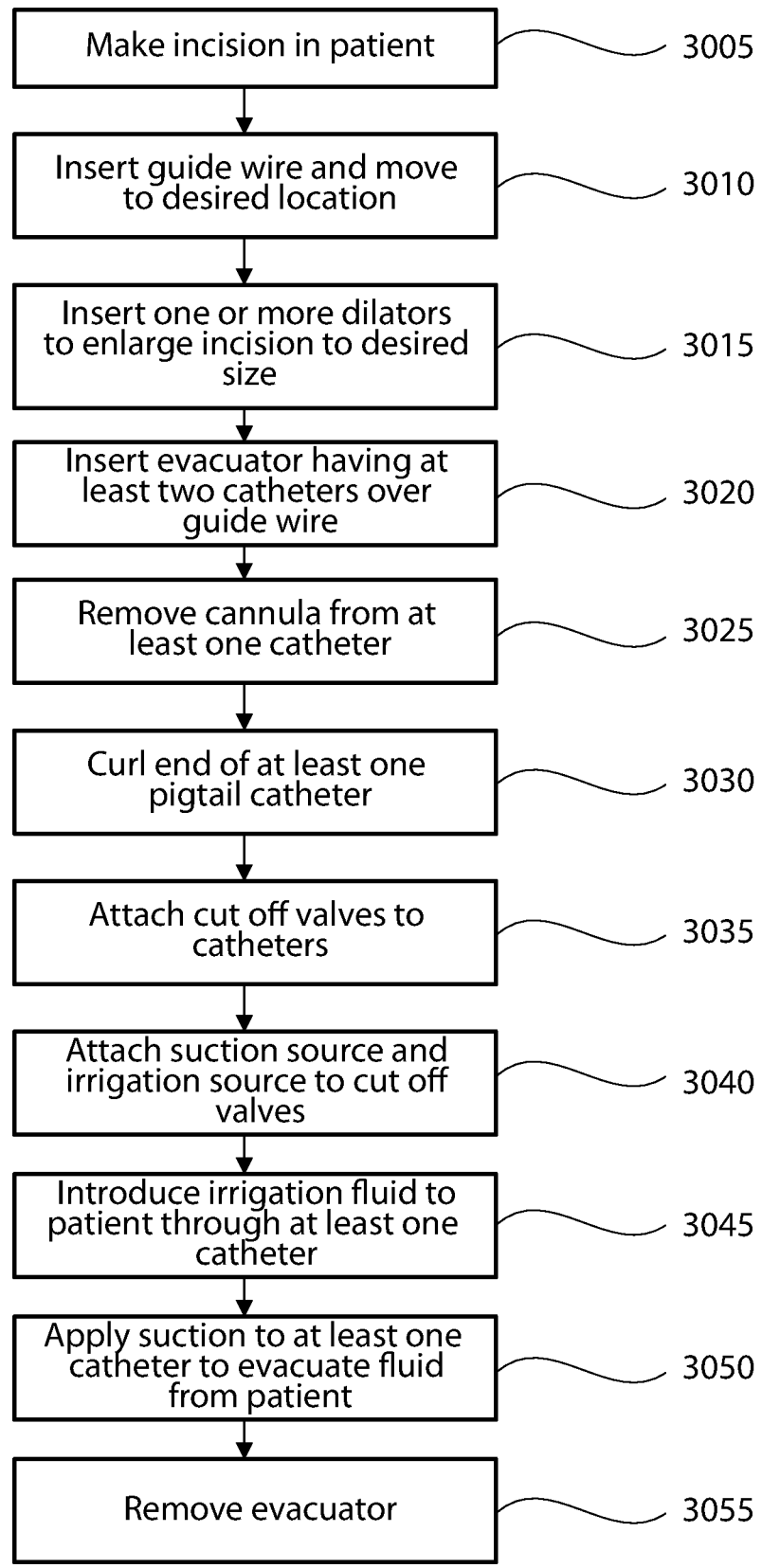
FIG. 30 is flow chart associated with a method of irrigating and draining a body cavity in accordance with another embodiment of the present invention.

FIGS. 29 and 30 are flow charts related to two exemplary methods of practicing the invention.

First, referring to FIG. 29, a first method will be described. In a first step, 2905, an incision is made in the patient. This may instead be the insertion of a hollow needle into the patient. At 2910 a guide wire is inserted into the incision (or through the hollow needle) and is moved to the desired position of the catheter device within the patient. In some embodiments a guide wire is not needed and is not used. One or more dilaters can be required to expand the incision to the required size so that the catheter device can fit into the incision. If required, the dilaters are inserted at 2915. At 2920 the catheter device comprising at least two catheters is inserted over the guide wire and moved into the desired position in the patient. Some embodiments include a sheath over the catheters. If such a sheath is used and it needs to be removed prior to use of the evacuator, the sheath is removed at 2925. In some embodiments, one or more of the catheters are pigtail catheters with ends that curl before use. If one or more of the catheters are pigtail catheters, the ends are curled at 2930. The curling of the catheters can be the catheters returning to their natural shape upon removal of the sheath or cannulas, or can be pulled into the curled configuration by some mechanical or other means. Some embodiments require the catheters to be inserted without the valves in place. For those embodiments, the valves are attached to the catheters at 2935. Each catheter will have a suction source, an irrigation source or a combination suction/irrigation source attached to the valve at 2940. In the cases where irrigation fluid is introduced into the patient, this is done at 2945. At 2950 suction is applied to one or more of the catheters to evacuate fluid from the patient through the catheters. After it is determined that the evacuator is no longer needed or otherwise needs to be removed, the evacuator is removed from the patient at 2955.

The method shown in FIG. 30 is in many ways similar to the method shown in FIG. 29, but applies to embodiments that do not use a sheath around the catheters. In FIG. 30 an incision is made in the patient at 3005 (or a hollow needle is inserted into the patient). At 3010 a guide wire is inserted into the incision (or into the hollow needle) and is moved to the desired position of the catheters of the catheter device. In some embodiments a guide wire is not needed and is not used. One or more dilaters can be required to expand the incision to the required size so that the evacuator can fit into the incision. If required, the dilaters are inserted at 3015. At 3020 the evacuator having at least two catheters is inserted over the guide wire and moved into the desired position in the patient. Some embodiments do not include a sheath over the catheters. If such a sheath is not used (or in some embodiments where a sheath is used) cannulas are inside one or more of the catheters to keep the catheters in a straight configuration for insertion into the patient. Any cannulas need to be removed prior to use of the catheters of the catheter device, and this is done at 3025. In some embodiments, one or more of the catheters are pigtail catheters with ends that curl before use. If one or more of the catheters are pigtail catheters, the ends are curled at 3030. The curling of the catheters can be the catheters returning to their natural shape upon removal of the cannulas, or can be pulled into the curled configuration by some mechanical or other means. Some embodiments require the catheters to be inserted without the valves in place. For those embodiments, the valves are attached to the catheters at 3035. Each catheter will have a suction source, an irrigation source or a combination suction/irrigation source attached to the valve at 3040. In the cases where irrigation fluid is introduced into the patient, this is done at 3045. At 3050 suction is applied to one or more of the catheters to evacuate fluid from the patient through the catheters. After it is determined that the evacuator is no longer needed or otherwise needs to be removed, the evacuator is removed from the patient at 3055.

The pigtail catheters described herein can be formed from various materials including, but not limited to, hydrophilic plastic, polyethylene, Vinyl, or the like. The cannulas described herein can be formed from various rigid materials including, but not limited to, hydrophilic plastic, polyethylene, Vinyl, metal, or the like. The sheath can be made from various materials including, but not limited to, hydrophilic plastic, polyethylene, Vinyl, or the like. Each of the aforementioned parts (i.e., the pigtail catheters, cannulas, and sheath) may be formed from other rigid materials such as other hard plastics, metal, or the like. Furthermore, in other embodiments one or more of the aforementioned parts may be formed from a solid, flexible material. Thus, variations in the material used to form the various components described herein are possible.

The examples described above use two pigtail catheters, but other embodiments can use three or more pigtail catheters or any combination of pigtail and non-pigtail catheters. Thus, it is noted that three or more of the pigtail catheters can also be used in a similar manner to that which has been described above with minor accommodations and modifications.

While the foregoing description and drawings represent exemplary embodiments of the present disclosure, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made within the scope of the present disclosure. One skilled in the art will further appreciate that the embodiments may be used with many modifications of structure, arrangement, proportions, sizes, materials, and components and otherwise, used in the practice of the disclosure, which are particularly adapted to specific environments and operative requirements without departing from the principles described herein. The presently disclosed embodiments are therefore to be considered in all respects as illustrative and not restrictive. The appended claims should be construed broadly, to include other variants and embodiments of the disclosure, which may be made by those skilled in the art without departing from the scope and range of equivalents. In addition, all combinations of any and all of the features described in the disclosure, in any combination, are part of the invention.

What is claimed is:

1. A body cavity irrigation and drainage system comprising:
    a catheter apparatus configured to be inserted into a pleural space of a patient, the catheter apparatus comprising:
        a body comprising a longitudinal axis and an inner surface that defines a cavity, the body being integrally formed as a monolithic structure;
        an internal wall located within the cavity that divides the cavity into a first flow channel and a second flow channel that are fluidly isolated from one another;
        wherein the body is alterable between: (1) a first state in which a distal portion of the body is elongated along the longitudinal axis; and (2) a second state in which the distal portion of the body is separated into a first tail portion that curls away from the longitudinal axis in a first direction and a second tail portion that curls away from the longitudinal axis in a second direction that is different than the first direction; and
        wherein the first tail portion defines a first distal portion of the first flow channel and the second tail portion defines a second distal portion of the second flow channel;
    an irrigation source operably coupled to the first flow channel of the catheter apparatus and configured to introduce a fluid into the pleural space through the first flow channel;
    a suction source operably coupled to the second flow channel of the catheter apparatus and configured to apply suction to the pleural space through the second flow channel; and
    wherein the first and second flow channels are fluidly isolated from one another such that the fluid is configured to be introduced into the pleural space through the first flow channel simultaneously with the suction being applied to the pleural space through the second flow channel.

2. The body cavity irrigation and drainage system according to claim 1 wherein the first distal portion of the first flow channel is fluidly isolated from the second distal portion of the second flow channel.

3. The body cavity irrigation and drainage system according to claim 1 wherein the internal wall comprises a first end coupled to the inner surface of the body on a first side of the longitudinal axis and a second end coupled to the inner surface of the body on a second side of the longitudinal axis, the first flow channel defined by a first surface of the internal wall and a first portion of the inner surface of the body, and the second flow channel defined by a second surface of the internal wall and a second portion of the inner surface of the body.

4. The body cavity irrigation and drainage system according to claim 1 further comprising a weakened section extending along the distal portion of the body, wherein the body is configured to tear along the weakened section to facilitate altering the body from the first state to the second state.

5. The body cavity irrigation and draining system according to claim 4 wherein the weakened section is formed along the body and the internal wall of the catheter apparatus so that the internal wall separates when the body is altered from the first state to the second state.

6. The body cavity irrigation and drainage system according to claim 1 wherein the first tail portion comprises a first portion of the internal wall and the second tail portion comprises a second portion of the internal wall.

7. The body cavity irrigation and drainage system according to claim 1 wherein the body of the catheter apparatus comprises a proximal end and a distal end, and wherein the internal wall extends an entirety of a length of the cavity form the proximal end to the distal end.

8. The body cavity irrigation and drainage system according to claim 1 wherein the body comprises a first longitudinal portion located on a first side of the longitudinal axis and a second longitudinal portion located on a second side of the longitudinal axis, and further comprising a first pull string coupled to the first longitudinal portion along the distal portion of the body and a second pull string coupled to the second longitudinal portion along the distal portion of the body.

9. The body cavity irrigation and drainage system according to claim 8 wherein the first and second pull strings are pulled in a direction away from the distal portion of the body to alter the body from the first state to the second state.

10. The body cavity irrigation and drainage system according to claim 1 wherein the body comprises a proximal end and a distal end, the body being elongated in a direction moving from the proximal end to the distal end, each of the first and second flow channels extending from the proximal end of the body to the distal end of the body.

11. The body cavity irrigation and drainage system according to claim 10 wherein the first and second flow channels are fluidly isolated from one another by the internal wall from the proximal end of the body to the distal end of the body.

12. The body cavity irrigation and drainage system according to claim 1 wherein the first and second tail portions extend in directions that are 180° from one another.

13. The body cavity irrigation and drainage system according to claim 1 wherein the fluid comprises saline.

14. The body cavity irrigation and drainage system according to claim 1 wherein the body comprises a first longitudinal portion located on a first side of the longitudinal axis and a second longitudinal portion located on a second side of the longitudinal axis, and further comprising a plurality of first apertures located along the distal portion of the first longitudinal portion of the body and a plurality of second apertures located along the distal portion of the second longitudinal portion of the body, wherein each of the first apertures forms an outlet of the first flow channel and wherein each of the second apertures forms an outlet of the second flow channel.

15. The boy cavity irrigation and drainage system according to claim 14 wherein the first apertures are located along the first tail portion of the body and the second apertures are located along the second tail portion of the body.

16. A system for irrigating and draining a pleural space of a patient, the system comprising:
a catheter apparatus comprising:
a tubular body having an inner surface that defines a cavity, a proximal end, a distal end, and a longitudinal axis extending between the proximal and distal ends;
a divider wall having a first end connected to the inner surface of the tubular body on a first side of the longitudinal axis and a second end connected to the inner surface of the tubular body on a second side of the longitudinal axis;
the cavity separated by the divider wall into a first flow channel defined by a first surface of the divider wall and a first portion of the inner surface of the tubular body and a second flow channel defined by a second surface of the divider wall and a second portion of the inner surface of the tubular body, the second flow channel being fluidly isolated from the first flow channel between the proximal and distal ends of the tubular body;
wherein the catheter apparatus is alterable between: (1) a first state in which the first and second flow channels are linear and parallel to the longitudinal axis along an entire length of the first and second flow channels from the proximal end to the distal end; and (2) a second state in which a distal portion of the first flow channel curls away from the longitudinal axis in a first direction and a distal portion of the second flow channel curls away from the longitudinal axis in a second direction that is different from the first direction:
an irrigation source operably coupled to the first flow channel of the catheter apparatus, wherein the irrigation source is configured to introduce a fluid into the pleural space through the first flow channel;
a suction source operably coupled to the second flow channel of the catheter apparatus, wherein the suction source is configured to apply suction to the pleural space through the second flow channel; and
wherein the first and second flow channels are fluidly isolated from one another such that the fluid is configured to be introduced into the pleural space through the first flow channel simultaneously with the suction being applied to the pleural space through the second flow channel.

17. The system according to claim 16 wherein the second direction is opposite the first direction.

18. The system according to claim 16 wherein the fluid comprises saline.

19. The system according to claim 16 wherein the catheter apparatus is configured to remove pus of a pleural empyema.

20. The system according to claim 16 further comprising at least one first aperture located along the distal portion of the catheter apparatus that provides a passageway into the first flow channel and at least one second aperture located along the distal portion of the catheter apparatus that provides a passageway into the second flow channel.

* * * * *